US006899715B1

(12) United States Patent
Beaty

(10) Patent No.: US 6,899,715 B1
(45) Date of Patent: May 31, 2005

(54) POWER-DRIVEN OSTEOTOME TOOLS FOR COMPACTION OF BONE TISSUE

(75) Inventor: Keith D. Beaty, Jupiter, FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 489 days.

(21) Appl. No.: 09/634,082

(22) Filed: Aug. 8, 2000

Related U.S. Application Data

(63) Continuation of application No. 09/232,362, filed on Jan. 15, 1999, now Pat. No. 6,171,312, which is a continuation of application No. PCT/US97/12512, filed on Jul. 17, 1997.

(60) Provisional application No. 60/022,148, filed on Jul. 18, 1996.

(51) Int. Cl.[7] .............................................. A61B 17/16
(52) U.S. Cl. ......................................... 606/80; 606/92
(58) Field of Search .............................. 606/32, 80, 84, 606/92, 93, 94, 102, 160; 600/471; 433/114, 433/118, 119, 144; 128/898

(56) References Cited

U.S. PATENT DOCUMENTS

| 2,328,270 A | 8/1943 | Greenberg ...................... 74/56 |
| 2,588,006 A | 3/1952 | Hufnagel ....................... 32/53 |
| 2,984,241 A | 5/1961 | Carlson ....................... 128/312 |
| 3,578,745 A | 5/1971 | Garnier ......................... 32/57 |
| 3,678,934 A | 7/1972 | Warfield et al. ............. 128/317 |
| 3,747,216 A | 7/1973 | Bassi et al. .................... 32/57 |
| 3,848,336 A | 11/1974 | Copeland ....................... 32/59 |
| 3,898,739 A * | 8/1975 | Gayso ......................... 433/119 |
| 3,921,044 A | 11/1975 | McShirley ................... 318/114 |
| 3,967,380 A | 7/1976 | Malata et al. ................... 32/27 |
| 3,969,823 A | 7/1976 | Nakanishi ....................... 32/27 |
| 4,173,828 A | 11/1979 | Lustig et al. ................. 433/87 |
| 4,185,383 A | 1/1980 | Heimke et al. ............. 433/173 |
| 4,248,232 A | 2/1981 | Engelbrecht et al. ....... 128/305 |
| 4,289,849 A | 9/1981 | Lustig et al. ............... 433/123 |
| 4,332,558 A | 6/1982 | Lustig .......................... 433/86 |
| 4,365,957 A * | 12/1982 | Das ............................ 433/144 |
| 4,392,827 A | 7/1983 | Martin ......................... 433/32 |
| 4,463,753 A | 8/1984 | Gustilo ..................... 128/92 B |
| 4,480,997 A | 11/1984 | Deutsch et al. ............. 433/221 |

(Continued)

FOREIGN PATENT DOCUMENTS

DE          296 06 335 U1     8/1996    ............ A61C 8/00

(Continued)

OTHER PUBLICATIONS

Summers, Robert B., DMD, "A New Concept In Maxillary Implant Surgery: The Osteotome Technique" (1994).

(Continued)

Primary Examiner—Julian W. Woo
(74) Attorney, Agent, or Firm—Jenkens & Gilchrist

(57) ABSTRACT

The invention set forth includes a set of tools which compact bone tissue as they develop a bore in the bone tissue and a driving mechanism for providing movement to the tools. The tools have engaging surfaces which displace bone tissue radially outward with respect to a central axis of the tool to create high density bone tissue at the wall defining the bore. The driving mechanism may provide only vibrational movement to assist in inserting the tool. Alternatively, the driving mechanism may provide translational movement in the longitudinal direction with respect to the tool to insert the tool into the bone.

50 Claims, 9 Drawing Sheets

U.S. PATENT DOCUMENTS

| | | | |
|---|---|---|---|
| 4,651,833 A | 3/1987 | Karpf et al. | 173/136 |
| 4,832,683 A * | 5/1989 | Idemoto et al. | 433/119 |
| 4,992,045 A | 2/1991 | Beisel | 433/32 |
| 5,019,083 A | 5/1991 | Klapper et al. | 606/99 |
| 5,026,387 A | 6/1991 | Thomas | 606/169 |
| 5,045,054 A | 9/1991 | Hood et al. | 604/22 |
| 5,151,030 A * | 9/1992 | Comeaux | 433/118 |
| D339,419 S | 9/1993 | Hood et al. | D24/146 |
| 5,242,302 A | 9/1993 | Riehm | 433/614 |
| D340,981 S | 11/1993 | Hood et al. | D24/146 |
| D341,201 S | 11/1993 | Hood et al. | D24/146 |
| D341,202 S | 11/1993 | Hood et al. | D24/146 |
| D342,313 S | 12/1993 | Hood et al. | D24/146 |
| 5,314,333 A | 5/1994 | Irmer et al. | 433/120 |
| 5,318,570 A | 6/1994 | Hood et al. | 606/99 |
| 5,324,297 A | 6/1994 | Hood et al. | 606/99 |
| 5,324,299 A | 6/1994 | Davison et al. | 606/167 |
| 5,443,468 A | 8/1995 | Johnson | 606/80 |
| 5,529,494 A * | 6/1996 | Vlacancich | 433/118 |
| 5,536,266 A * | 7/1996 | Young et al. | 606/92 |
| 5,569,035 A | 10/1996 | Balfour et al. | 433/165 |
| 5,573,537 A | 11/1996 | Rogozinski | 606/80 |
| 5,575,650 A | 11/1996 | Niznick et al. | 433/165 |
| 5,577,911 A * | 11/1996 | Garfinkel | 433/119 |
| 5,586,989 A * | 12/1996 | Bray, Jr. | 606/160 |
| 5,676,545 A | 10/1997 | Jones | 433/165 |
| 5,713,736 A | 2/1998 | Heath | 433/102 |
| 5,718,707 A | 2/1998 | Mikhail | 606/94 |
| 5,839,897 A | 11/1998 | Bordes | 433/165 |
| 5,897,560 A * | 4/1999 | Johnson | 606/102 |
| 6,139,320 A * | 10/2000 | Hahn | 433/119 |

FOREIGN PATENT DOCUMENTS

| | | | |
|---|---|---|---|
| WO | WO 95/21590 | 8/1995 | A61C 8/00 |

OTHER PUBLICATIONS

Summers, Robert B., DMD, "The Osteotome Technique: Part 2—The Ridge Expansion Osteotomy (REO) Procedure" (1994).

Summers, Robert B., DMD, "The Osteotome Technique: Part 3—Less Invasive Methods Of Elevating The Sinus Floor" (1994).

Implant Innovations, Inc., Brochure, Surgical Catalog (no date).

Instrument Makar, Inc., "Issues In ACL Reconstruction" (no date).

Brooks, Andrew T., MD, et al., "Effect Of An Ultrasonic Device On Temperatures Generated In Bone And On Bone—Cement Structure,"*The Journal Of Arthroplasty*, vol. 8, No. 4, pp. 413-418 (Aug. 1993).

Caillouette, James T., MD, et al., "Revision Arthroplasty Facilitated By Ultrasonic Tool Cement Removal—Part I: In Vitro Evaluation,"*Orthopaedic Review*, vol. XX, No. 4, pp. 353-357 (Apr. 1991).

Caillouette, James T., MD, et al., "Revision Arthroplasty Facilitated By Ultrasonic Tool Cement Removal—Part II: Histologic Analysis Of Endosteal Bone After Cement Removal,"*Orthopaedic Review*, vol. XX, No. 5, pp. 435-440 (May 1991).

Frankel, Andrew, MD, et al., "Ultrasound For Revision Hip Arthroplasty,"*Current Science*, pp. 43-45 (1993).

Gardiner, Robert, MD, et al., "Revision Total Hip Arthroplasty Using Ultrasonically Driven Tools,"*The Journal Of Arthroplasty*, vol. 8, No. 5, pp. 517-521 (Oct. 1993).

Klapper, Robert C., M.D., "The Use Of Ultrasonic Tools In Revision Arhtroplasty Procedures," 7 pages (no date).

Product Literature for ULTRA-DRIVE® Illumination System, Biomet, Inc., 2 pages (1993).

* cited by examiner

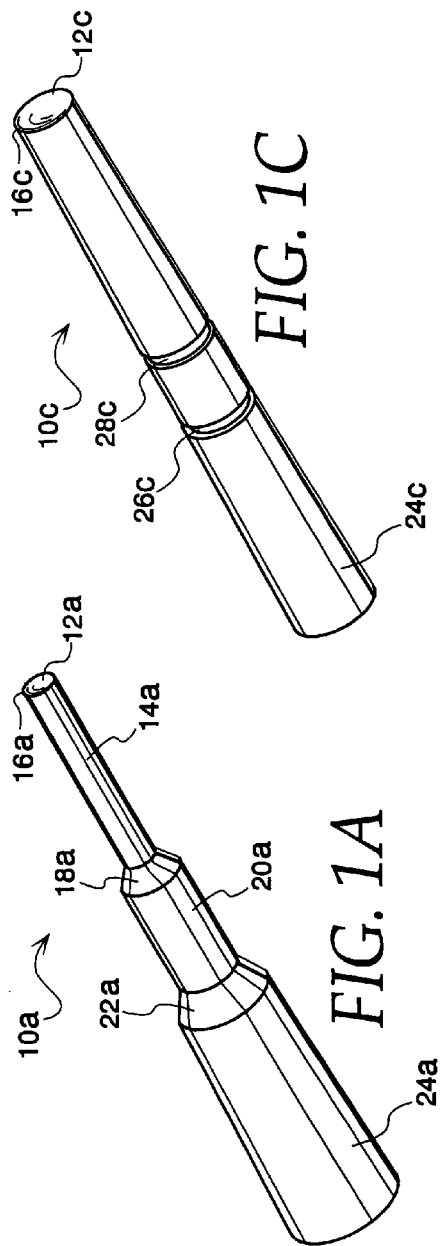
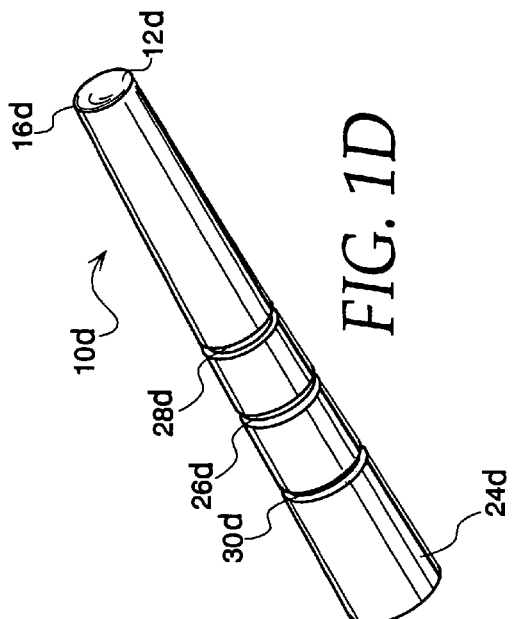
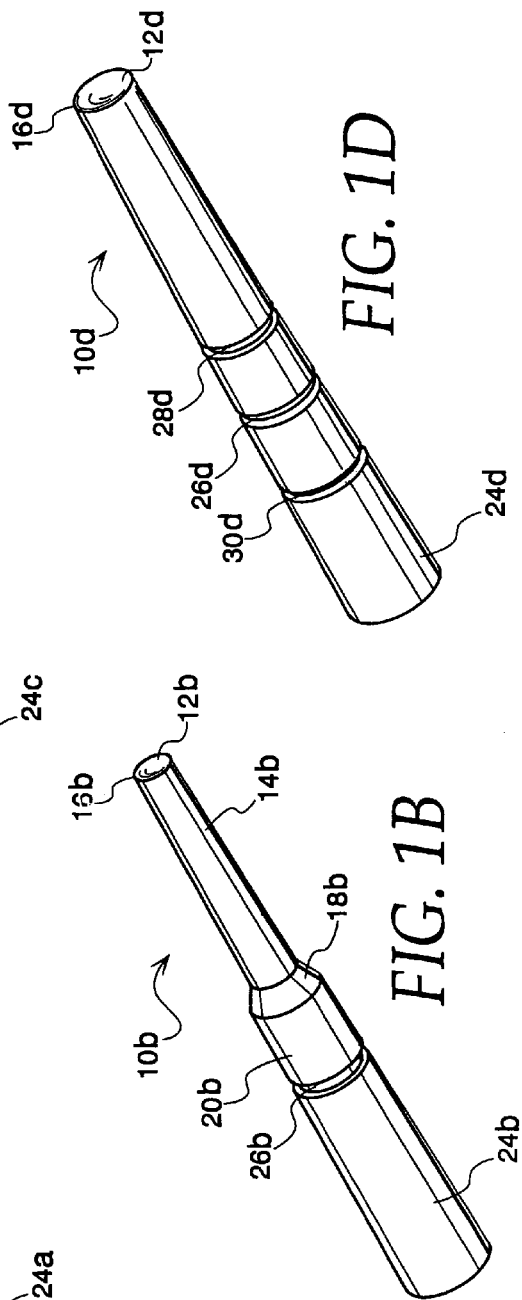

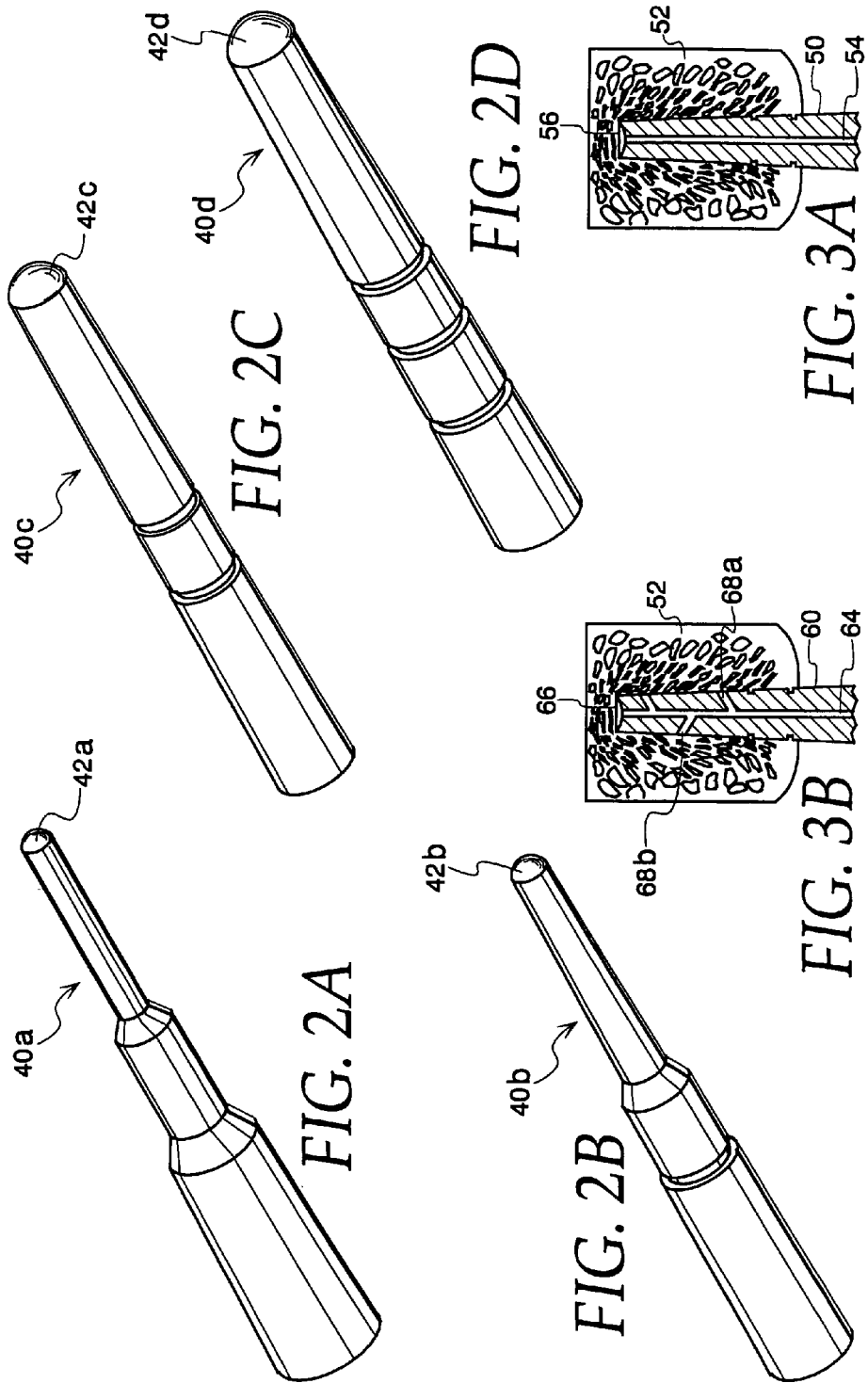

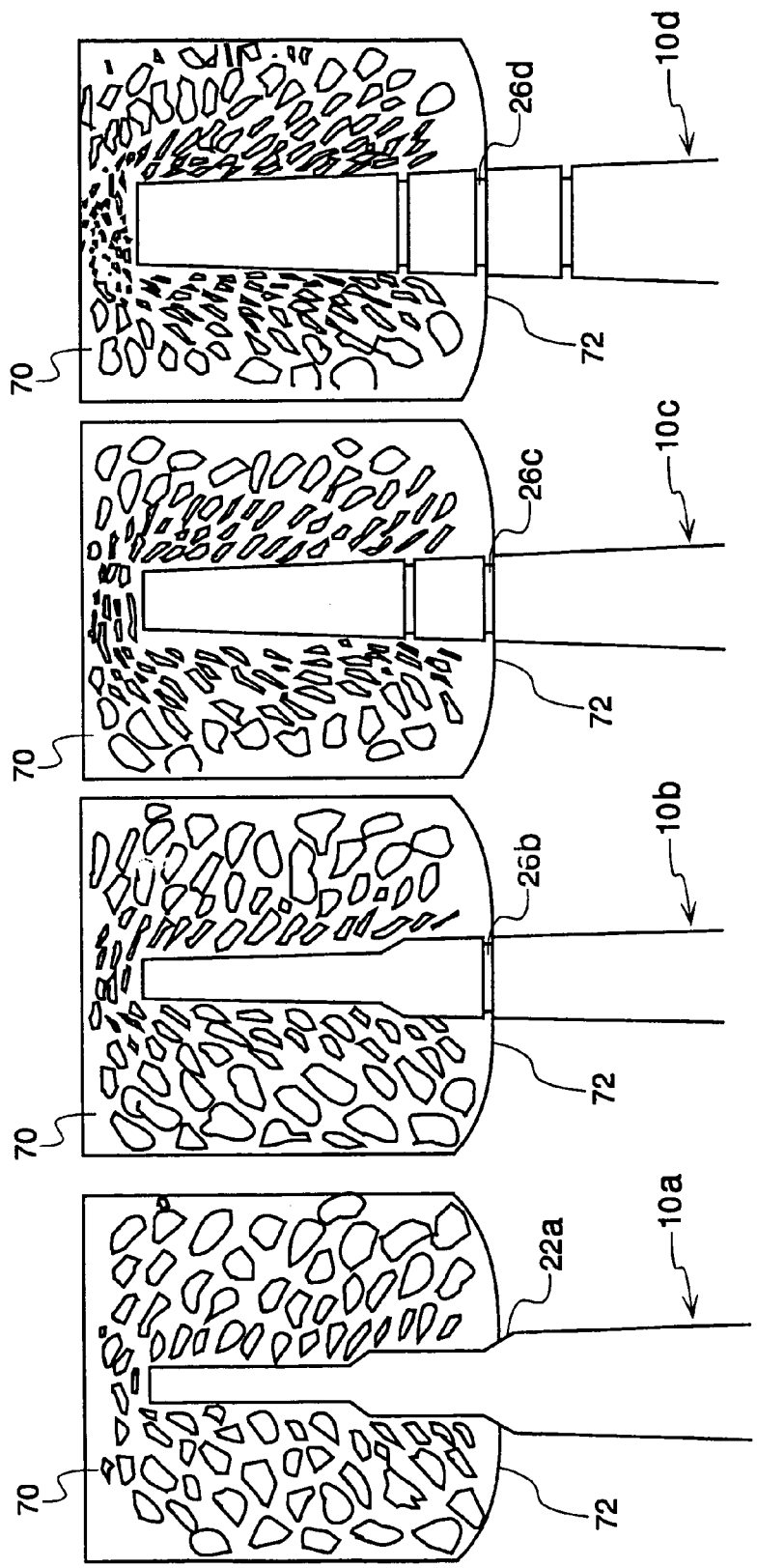

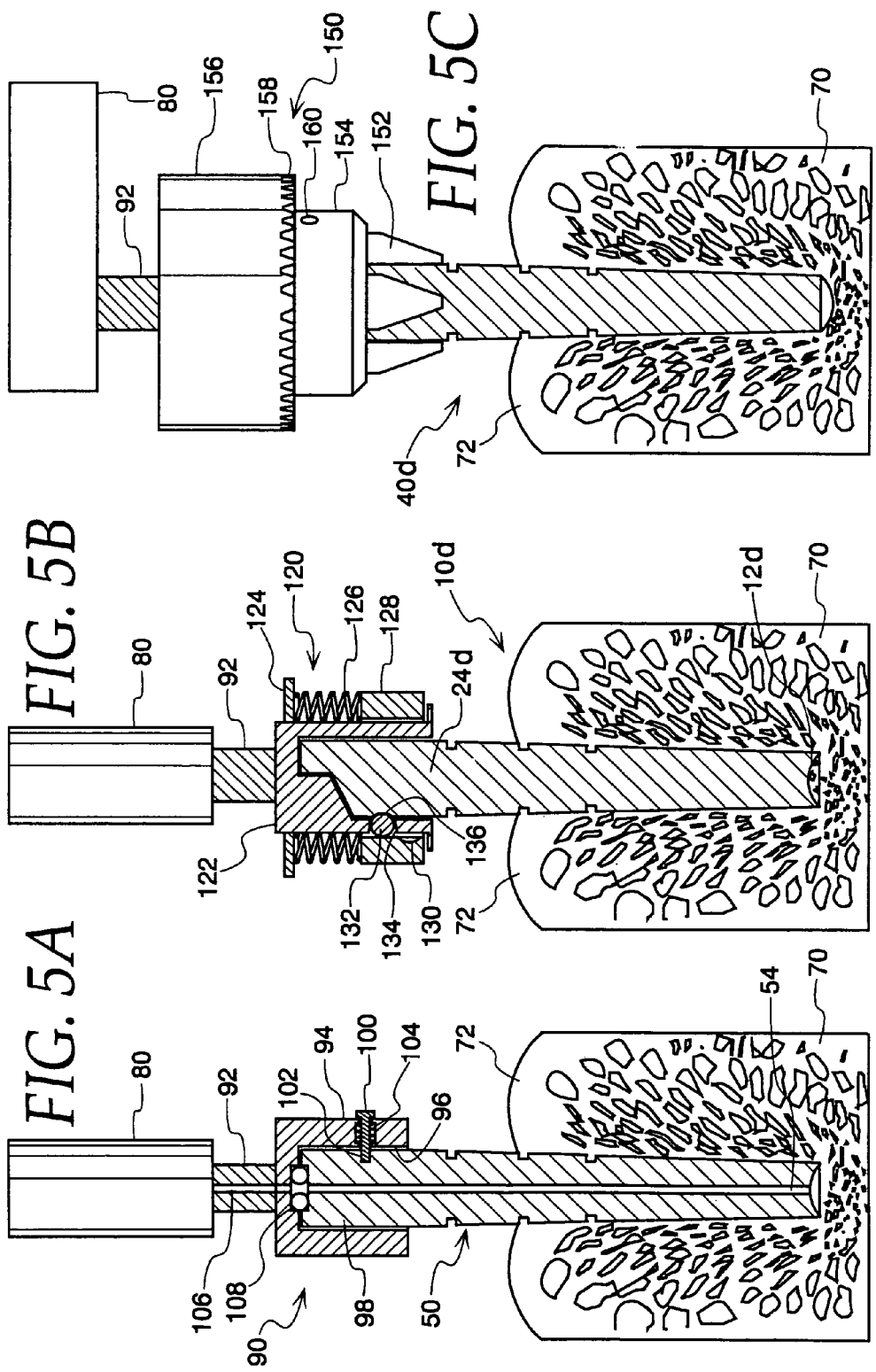

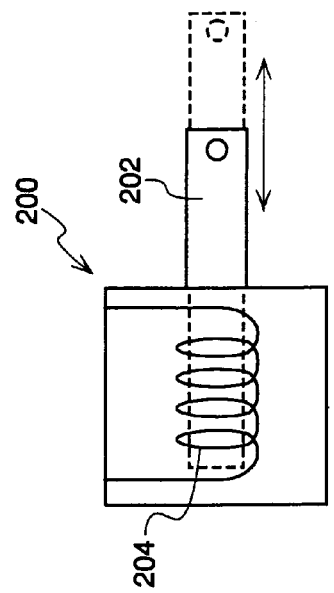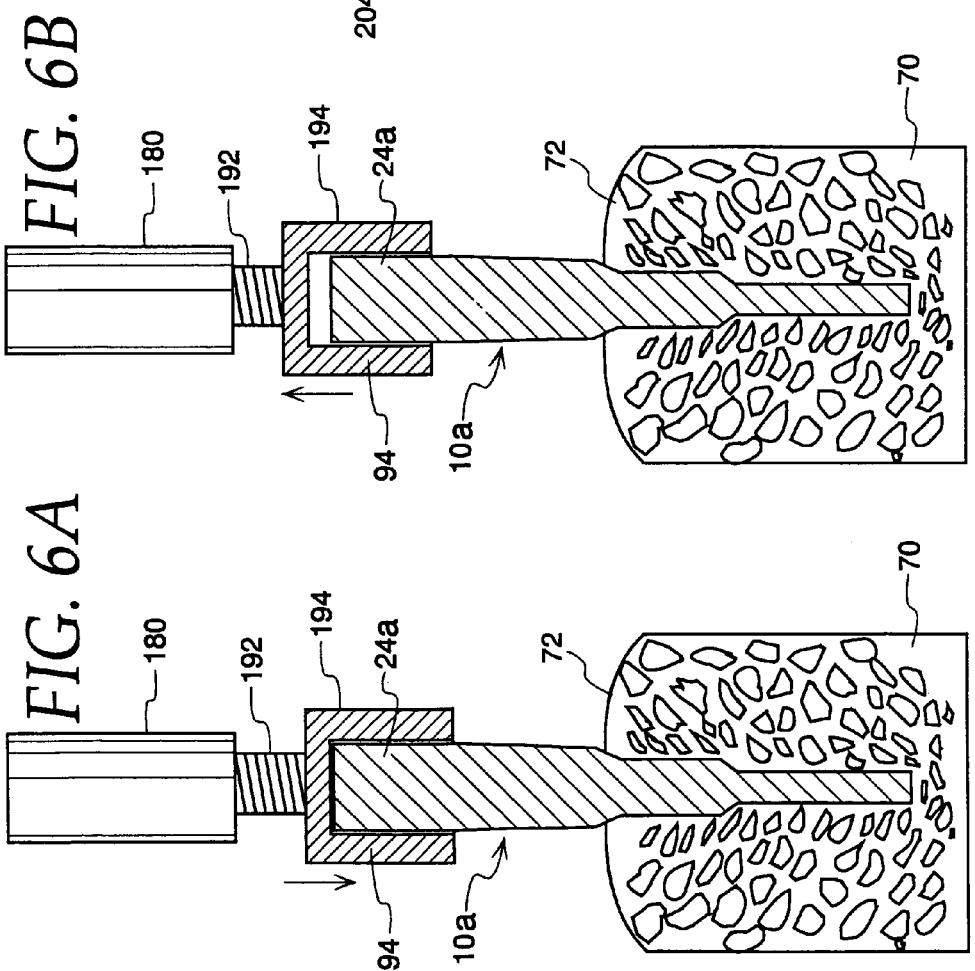

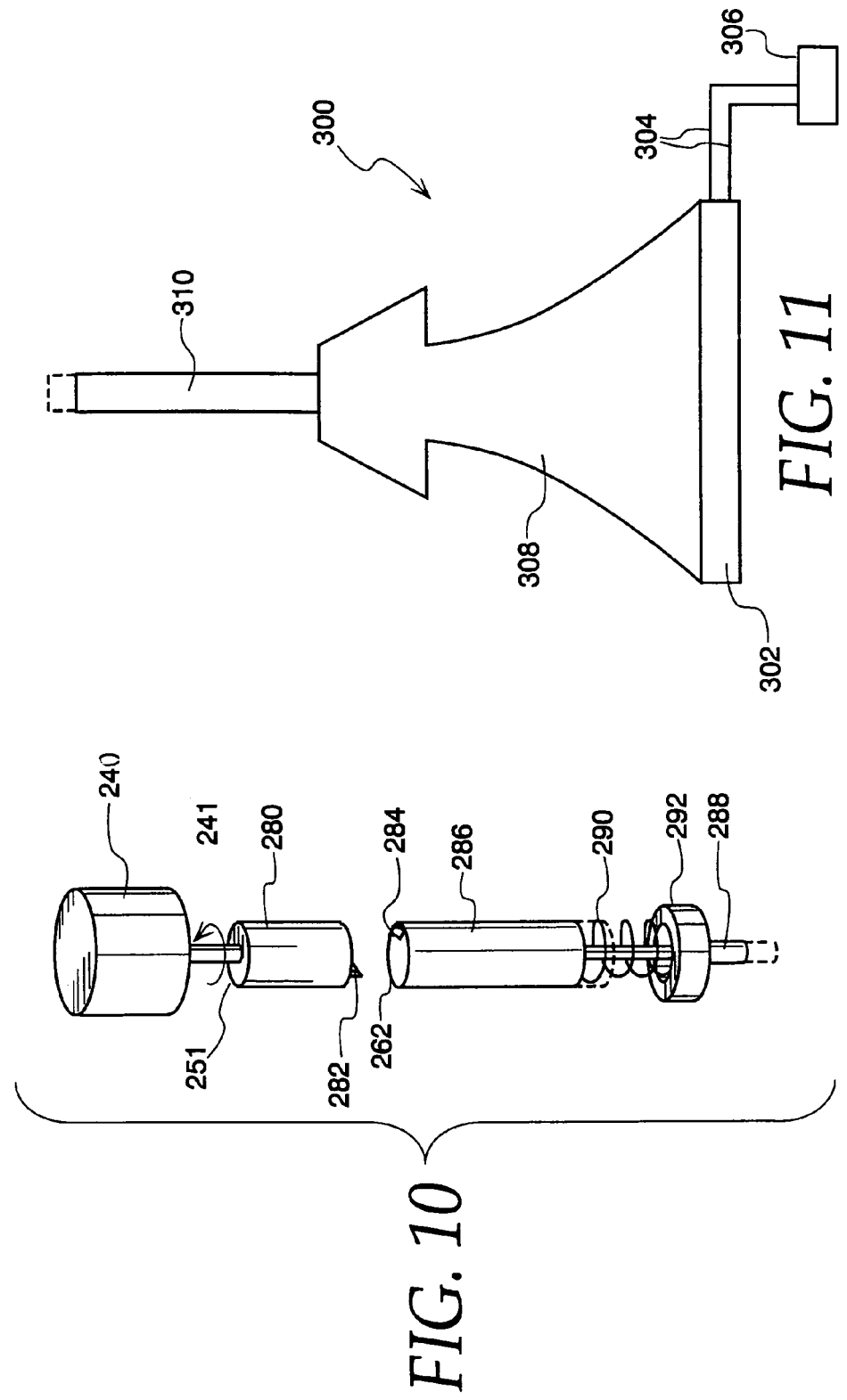

US 6,899,715 B1

POWER-DRIVEN OSTEOTOME TOOLS FOR COMPACTION OF BONE TISSUE

CROSS REFERENCES TO RELATED APPLICATIONS

This application is a continuation of application Ser. No. 09/232,362, filed Jan. 15, 1999, now U.S. Pat. No. 6,171,312; which is a complete application claiming the benefit of continuation copending International Patent Application No. PCT/US97/12512, filed Jul. 17, 1997 which claims the benefit of provisional application 60/022,148 file Jul. 18, 1996.

FIELD OF THE INVENTION

The invention relates to an apparatus for preparing a bore in living bone. Specifically, the apparatus produces a bore in bone via an osteotome or compaction technique whereby bone is compacted into the side walls and the bottom wall defining the bore instead of being extracted from the bore as is typical during drilling techniques.

SUMMARY OF THE INVENTION

In one embodiment, a combination includes a plurality of tools for insertion into the bone to produce a bore at a site where an implant is to be installed and a mechanism for driving those tools. The plurality of tools have portions with the same basic shape but with progressively larger diameters. A set of tools may also include tools having variable shapes as well. Each tool has surfaces which urge the displaced bone radially outward and compress the displaced bone into the wall defining the bore. The driving mechanism can be one of a variety of types including, among many, electromagnetic-powered devices, hydraulically-powered devices, motor-driven devices, pneumatically-powered devices, and piezoelectric-powered devices.

The tools are coupled to the driving mechanism in series with the smallest being coupled first. The driving mechanism applies the necessary force to insert the tool into the bone. The driving mechanism can be operated in various ways. In one embodiment, the operator continuously moves the driving mechanism toward the bone to engage and contact the tool and to push it further into the bore. Such a driving mechanism has a portion for engaging the tool that undergoes reciprocating movement to "tap" the tool into the bore. The tool is not attached to the driving mechanism in this configuration, but is repetitiously engaged by the driving mechanism.

Alternatively, the driving mechanism includes a shaft that is attached to the tool. The shaft of the driving mechanism causes gradual, steady movement of the tool as it is inserted into the bore. Instead of this gradual movement, this movement imparted on the tool can be incremental or stepped. And, the steady movement can be supplemented by high-frequency vibration to further assist in the insertion of the tools To further enhance the system, a controller can be used to provide for a more accurate insertion of the tools. For example, the controller may control the depth of insertion, the frequency of reciprocating motion, or the force of insertion.

The driving mechanism may also be modular in that it could be used to insert the dental implant into the bore after the tools have provided the appropriately sized bore. Thus, the shaft of the driving mechanism has means to engage the top portion of a self-tapping implant and screws the implant into the bore. The engaging means may also interface with a tap that is used prior to the insertion of a non-self-tapping implant. Lastly, the engaging means may be coupled to the top portion of a non-threaded implant which is pushed into the bore.

BRIEF DESCRIPTION OF THE DRAWINGS

FIGS. 1A–1D illustrate a series of osteotome tools having inwardly concave ends;

FIGS. 2A–2D illustrate a series of osteotome tools having outwardly convex ends;

FIGS. 3A–3B illustrate an osteotome tool having an internal fluid channel along its axis;

FIGS. 4A–4D illustrate four progressive insertions of four progressively larger osteotome tools;

FIGS. 5A–5C illustrate clamping mechanisms for coupling the osteotome tool to the driving mechanism;

FIGS. 6A–6B illustrate a driving mechanism producing reciprocating motion that is used to insert the tool into the bone;

FIG. 7 illustrates a solenoid as the driving mechanism;

FIG. 10 illustrates an electric motor as the driving mechanism which produces stepped translational motion through another cam configuration;

FIG. 11 illustrates a piezoelectric translator driving mechanism;

DETAILED DESCRIPTION OF THE DRAWINGS

Figure 9:
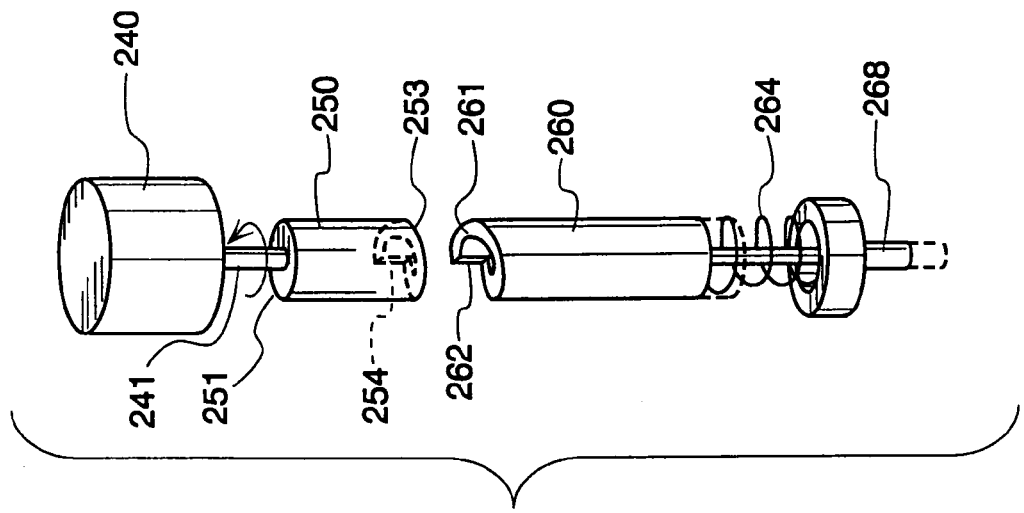
FIG. 9 illustrates an electric motor as the driving mechanism which produces translational motion through a cam configuration.

Referring initially to FIGS. 1A–1D, a set of osteotome tools 10a–10d is illustrated. Tool 10a is the smallest and is the first tool to be inserted into the bone. Often, the use of tool 10a is preceded by the use of a small drill that produces a pilot hole. Tool 10a includes an inwardly concave face 12a and a narrow first portion 14a adjacent the concave face 12a. The first portion 14a and the concave face 12a meet at an edge 16a. First portion 14a may be a constant diameter as shown or it may taper outwardly in a direction away from concave face 12a. In a preferred embodiment, the diameter of the first portion 14a is slightly larger (e.g. about 0.2 mm to 1.0 mm larger) than the pilot hole of the bore.

Because the cortical bone is very dense, there is a chance that it could fracture during insertion of the tools. Thus, it may be beneficial to expand the pilot hole at the cortical bone to prevent such a fracture. This expansion can be accomplished through the use of a cutting tool, such as a burr, positioned at the pilot hole prior to insertion of the osteotome tools.

Any bone tissue on the walls defining the pilot hole that is engaged by the edge 16a is pushed into concave portion 12a where it collects. In essence, the edge 16a "shaves" off a portion of the bone tissue along the wall defining the pilot hole. When the tool 10a has reached its maximum depth in the bore and is pulled from the bore, the collected material typically remains at the bottom of the bore. Thus, because the edges 16b remove a portion of the bone tissue and the concave face 12b collects this tissue and displaces it downwardly, the osteotome tool 10a provides a local bone graft. When the osteotome is used in the jawbone, displacing the cancellous bone tissue within the jawbone to the bottom of the bore is advantageous to increase the amount of bone tissue adjacent to the sinus cavity as is described below.

Transition surface 18a serves to rapidly force the bone tissue outwardly along the wall defining the bore. Thus, transition surface 18a acts upon the wall to substantially widen it and form a bore of a larger diameter. Because the transition surface 18a is positioned at a distance from the edge 16a of the tool 10a, only a portion of the bore encounters the rapid expansion.

Intermediate portion 20a is positioned adjacent to the transition surface 18a. Intermediate portion 20a may be a constant diameter as shown or taper outwardly in a direction way from the concave face 12a. Intermediate portion 20a firms the wall of the bore as tool 10a is inserted into the bore. As with the transition surface 18a, the intermediate portion 20a only engages an axial portion of the bore.

A second transition surface 22a is inserted into the bore to further push the walls outwardly near the opening of the bore. This serves to further open the bore at the surface of the bone such that the faces 12b–12d of the next tools 10b–10d can be inserted with ease.

A base portion 24a generally does not enter the bore. Instead it is the portion of the tool 10a to which the driving mechanism is coupled as is described in detail below.

In situations where it is desired to widen the ridge of the jawbone, the base portion 24a and, therefore, the second transition surface 22a can be inserted into the upper portion of the bore to begin the ridge-widening process. This ridge-widening process is augmented by the insertion of the tools 10b–10d which have wider diameters.

By displacing bone that was once in the central portion of the bore, the transition surfaces 18a and 22a and the intermediate portion 20a also act as local bone grafting tools. This localized bone grafting process provides a bore with a wall having high-density bone tissue.

FIG. 1B illustrates another tool 10b having a slightly larger diameter than tool 10a in FIG 1A. The inwardly concave face 12b meets the first portion 14b at edge 16b which serves to "shave" off an additional section of the wall defining the bore. Transition portion 18b forces the bone tissue outwardly to compact and form a wall with a larger diameter. Again, transition portion 18b provides a substantial widening of the bore as did transition portions 18a and 22a of tool 10a. Intermediate portion 20b compacts the wall as it advances down the length of the bore. There is no second transition portion in tool 10b as there is at reference numeral 22a in tool 10a of FIG. 1A, although there could be. Base portion 24b is the portion to which the driving mechanism is coupled.

Tool 10b also includes a depth mark 26b which indicates the appropriate depth to which the tool 10b should be inserted. The depth park 26b is positioned from the edge 16b of the tool 10b at about the same distance as the transition portion 22a is positioned from the edge 16a of tool 10a. Depth mark 26b typically corresponds to the length of the implant that is to be inserted. As will be seen in FIGS. 1C and 1D, tools 10c and 10d include depth marks at corresponding heights to assist the clinician in determining the correct depth of insertion. Because different bone regions require implants of different length, a different set of osteotome tools can be used that have different lengths and corresponding depth marks. Alternatively, an osteotome tool set may have marks at various depths so that they can be used for implants of various lengths.

The osteotome tools 10c and 10d of FIGS. 1C and 1D are similar to the tools 10a and 10b in that they have inwardly concave faces 12c and 12d and edges 16c and 16d. However, tools 10c and 10d do not include a transition portion. Thus, transition portion 18b of tool 10b is the last surface to quickly expand the diameter of the bore.

The first portions 14c and 14d of these tools 10c and 10d taper outwardly to gradually increase the diameter of the bore as they are inserted therein. The driving mechanism is to be coupled to the base portions 24c and 24d of tools 14c and 14d.

Tool 10c has a pair of depth marks 26c and 28c. Depth mark 26c is at about the same distance from edge 16c as depth mark 26b is from edge 16b in FIG. 1B. Depth mark 28c is approximately at the same distance from edge 16c as the transition portion 18b is from edge 16b in FIG. 2.

Tool 10d includes depth marks 26d and 28d that correspond, respectively, to depth mark 26c and 28c of tool 10c in FIG. 1C. An additional depth mark 30d is positioned near the base portion 26d at a predetermined distance from depth mark 26d.

The concave faces 12a–12d are shown having a smooth, inwardly concave surface. Alternatively, the faces 12a–12d may have a sharp focus point such that the surface is not smooth, or have a back surface that is in a plane that is approximately parallel to the plane defined by edges 16a–16d in tools 10a–10d, respectively.

The osteotome tools 10a to 10d are typically made of a metal such as titanium or stainless steel (e.g. a 400-series stainless steel). Thus, they can be sterilized and reused. Alternatively, the tools 10a to 10d can be made of a polymeric material that can be discarded after each use. The polymeric material must be chosen to provide the necessary strength to allow the cutting action at the edge near the concave face.

Osteotome tools maintain nearly all of the displaced bone tissue within the bore such that only an insubstantial amount is removed therefrom. This is primarily accomplished by the concave faces at the ends of the tool which collect the bone tissue shaved from the walls defining the bore and move that bone tissue deeper within the bore. Additionally, the osteotome tools force the bone tissue radially outward to create a more dense wall. Thus, some of the bone tissue that is in the region that subsequently becomes the bore is displaced radially outward while some of the bone tissue is displaced to a different depth in the bore. Moreover, extraction of the tool has a minimal effect on the bore wall. Consequently, the wall defining the bore is more dense which helps to stabilize the implant within the bore, promote osseointegration, and provide for a more even distribution of stresses onto the walls of the bore caused by the loading of dental components attached to the implant. However, the density of the bone is not made so large that the flow of blood to the bone tissue is substantially inhibited which hinders or possibly precludes the healing process. Instead, the bone density is such that blood flows to the tissue at a rate that promotes the healing of the tissue and osseointegration with the implant.

This osteotome technique is also useful in regions where the bone density is lower than average. This technique increases the density of the bone tissue in these low-density regions that are immediately adjacent to the bore to a point that is near average, or even above average density. Thus, in low-density regions, an implant placed into a bore produced by this osteotome technique is more stable than one that is placed in a bore produced by common drilling techniques.

In a preferred embodiment using the power-driven osteotome technique in the jawbone, the less dense bone, commonly referred to as Type III and Type IV bone tissue, can be compacted such that its density would be comparable to Type I or Type II bone tissue which is usually associated with the more dense cortical plates. However, the compacted bone tissue should not exceed the density of Type I bone. Density values above that of Type I bone could compromise the vascularization and remodeling of the newly packed bone tissue which can lead to a vascular necrosis resulting from inadequate fluid transport across the newly packed region.

Utilizing the osteotome tools 10a–10d also permits the raising of the sinus floor. As the bone is shaved from the side walls, the displaced bone is moved upwardly toward the sinus cavity by the concave faces 12a–12d. This build-up of the bone mass near the sinus boundary elevates the sinus floor, the periosteum, and the membrane layer. Because of the volume of bone located at the bottom of the tools adjacent to the concave faces 12a–12d, the end of the tool typically does not contact the sinus membrane. Instead, the displaced bone tissue engages this membrane. Often, the end of the tool does not penetrate past the original sinus boundary. However, whether the tool engages the membranes depends on the geometry of the concave faces 12a–12d (i.e. the volume of bone which can be contained in that face). If additional bone is needed to elevate the sinus floor, a prepared bone mixture can be added to the bore and pushed upwardly with the shaved bone by the concave faces 12a–12d to provide for additional elevation. Utilization of the osteotome tools produces minimal heat in comparison with common drilling techniques which elevates the local bone tissue temperature due to the high friction at the cutting surfaces of the flutes. Elevated temperatures can damage the bone tissue and slow osseointegration. Thus, the use of the osteotome tools also enhances the quality of the bone tissue adjacent the implant.

FIGS. 2A–2D illustrate another type of osteotome tool 40a–40d. The tools 40a–40d are essentially the same as those shown in FIGS. 1A–1D except that the faces 42a–42d are outwardly convex. This shape is not conducive to carrying bone tissue that is shaved from the sides of the wall. Instead, the outwardly convex faces 42a–42d push the bone outwardly into the wall defining the bore. Because no bone tissue is being shaved from the walls and transported further into the bore, the diameter of the face 42a on tool 40a may be approximately the same or less than the diameter of a pilot hole if one is used. The tool 40a may then taper beyond face 42a to a diameter larger than the diameter of the pilot hole to force the bone tissue radially outward. Although the shape is shown as outwardly convex with a smooth point, it may also be curved with a sharp point. Alternatively, the convex faces 42a–42d may by merely conical in that they come to a sharp point. In yet a further alternative, the outwardly convex faces 42a–42d may have a small dimple at their extremities to displace a small amount of bone tissue inwardly.

FIGS. 3A–3B show yet another type of osteotome tool. In FIG. 3A, osteotome tool 50, shown in bone tissue 52, includes an internal channel 54 in which a fluid (liquid or gas) is carried to the face 56 of the tool 50. The fluid serves to lubricate the bore prior to, or concurrently with, the cutting process that occurs at the edge. The fluid may be an agent which promotes the growth of bone tissue to enhance the osseointegration of the implant around the bore. The channel 54 also assists in removing the collected bone tissue in face 56 in that applying pressure to the channel 54 expels the collected bone tissue from the face 56.

The osteotome tool 60 in FIG. 3B is similar to tool 50 of FIG. 3B except that the internal channel 64 carries fluid not only to the face 66, but to side exits 68a and 68b. Thus, the lubrication can also be provided to the bone tissue 52 at the sides of the tool 60.

FIGS. 4A–4D illustrate the process by which the osteotome tools 10a–10d of FIGS. 1A–1D are inserted into bone tissue 70. In FIG. 4A, the tool 10a is inserted into the bone tissue 70 to a point where second transition 22a meets the upper surface 72 of the bone tissue 70. As stated previously, tool 10a, which has a smaller diameter than the remaining tools 10b–10d, is typically inserted into a small diameter pilot hole. Tool 10b, shown in FIG. 4B, is then inserted until depth mark 26b reaches the upper surface 72.

Tool 10c, shown in FIG. 4C, is inserted until depth mark 26c reaches the upper surface 72 to further expand the bore and provide more compaction of the wall defining the bore. Lastly, tool 10d is inserted into the bore until depth mark 26d reaches the upper surface 72. Tool 10d, shown in FIG. 4D, provides the last compaction of the wall defining the bore prior to the insertion of the implant.

Although the process of FIGS. 4A–4D has been described as using four osteotome tools, the process may require more or less tools depending on the size of the bore that is desired. Additionally, if the diametric difference between successive osteotome tools is kept to a minimum (e.g. less than 0.5 mm difference in diameter), then the amount of force needed to insert the tools is decreased since each tool will be displacing only a small amount of bone. But, this also increases the number of tools required and may increase the overall time required to produce the bore.

Thus far, the osteotome tools and their advantages have been described. FIGS. 5–14 relate to the interaction between the driving mechanism and the osteotome tools. Two basic methods exist for coupling the action of the driving mechanism to the osteotome tools. First, the osteotome tool can be directly attached to the driving mechanism such that any movement, such as vibrational or longitudinal movement, produced by the driving mechanism translates into the same movement of the osteotome tool. And second, the osteotome tool can be engaged repetitiously by reciprocating movement produced by the driving mechanism such that the tool is tapped, or hammered, into the bore.

FIGS. 5A–5C illustrate three methods in which the osteotome tool is coupled to a driving mechanism 80. Each of these methods provides direct attachment of the osteotome tool to the driving mechanism such that any movement by the driving mechanism causes the same movement of the tool. The various types of driving mechanisms 80 will be described in detail with reference to FIGS. 7–14.

In FIG. 5A, the osteotome tool 50 shown in FIG. 3A having internal channel 54 is coupled to a clamping mechanism 90. The clamping mechanism 90 is coupled to a driving mechanism 80 via a shaft 92. The clamping mechanism 90 includes a cylinder 94 with an inner wall 96 defining an opening into which the base portion 98 of the tool 50 is attached. A pin 100 extends through a wall of the cylinder 94 and enters a hole 102 in the tool 50. Thus, when the base portion 98 of the tool 50 is inserted into the cylinder 94, it is held captive there by the pin 100. Typically, the pin 100 is biased by a spring 104. Thus, the clinician works against the force of the spring 104 when pulling the pin 100 radially outward so as to remove or insert the tool 50.

Although the pin 100 is shown extending into the base portion 98 of the tool 50, a pin could be used that extends through the entire base portion 98. For example, a basic cotter pin could be employed which removes the need for the spring 104. In yet another alternative, the pin 100 is replaced by a screw which can be manipulated by hand. The hole 102 then is internally threaded to accommodate the screw. Rotation of the screw causes it to engage the base portion 98 and clamps the tool 50 within the cylinder 94.

It should also be noted that the cylinder 94 could simply be a plurality of fingers extending downwardly. One of the fingers must have a width that would allow it to accommodate the pin or screw configurations.

To accommodate the passage of fluid through channel 54, the shaft 92 includes a passageway 106 which is coupled to the channel 54 at the top of the base portion 98 of the tool 50. Furthermore, an O-ring 108 acts to seal the interface between the channel 54 and the passageway 106. A fluid supply device (not shown), for example a manual bulb pump or an automatic pump, is coupled to the passageway 106 in the shaft 92 to provide for the flow of fluid through the tool 50.

The driving mechanism 80 acts to move shaft 92 in a direction substantially parallel to the axis of the tool 50 such that the tool 50 is pushed inwardly into the bore. As stated previously, the amount of movement of the shaft 92 dictates the movement of the tool 50. The movement of the shaft 92 can be steady such that the tool 50 is inserted at a constant rate. Alternatively, the shaft 92 can be moved downward through incremental, or stepped, movement or the shaft 92 may simply vibrate due to the vibrational energy produced by the driving mechanism 80. After the tool 50 is inserted to the appropriate depth, the driving mechanism 80 is then reversed and the tool 50 is extracted from the bone tissue 70 or the clinician may simply pull the entire assembly from the bore.

The shaft 92 extends into the driving mechanism 80 and moves outwardly therefrom when the driving mechanism 80 is operational. The shaft 92 can also be telescopic such that its portion extending into the driving mechanism 80 does not have to be the same length as the depth of the bore. Consequently, the driving mechanism 80 can be designed such that it occupies a smaller volume.

FIG. 5B illustrates a ball-slot clamping mechanism 120, commonly known as a Yankee-style clamp, that is coupled to tool 10*d* illustrated in FIG. 1D. The tool 10*d* is shown fully inserted into the bore with the inwardly-concave face 12*d* containing bone tissue. The ball-slot clamping mechanism 120 includes a cylinder 122 that is attached to shaft 92 of the driving mechanism 80. A platform 124 projects from the cylinder 122. At least one spring 126 is disposed between the bottom side of the platform 124 and a slidable ring 128 that surrounds the cylinder 122. The spring 126 acts on the ring 128 to bias it in the downward direction away from the platform 124.

The ring 128 includes a divot 130 in the shape of a spherical segment. A small sphere 132, possibly a ball bearing, is positioned within an opening 134 in the cylinder 122. The opening 134 is such that the sphere 132 can only partially enter into the cavity of the cylinder 122 and move radially outward into the divot 130. The shape of the divot 130 corresponds to the shape of the small sphere 132 that is positioned against the inside wall of the ring 128.

The tool 10*d* has been modified slightly as it is shown in FIG. 1D to also include a second divot 136 having a shape similar to divot 130 on the ring 128. Also, tool 10*d* has its upper portion 24*d* modified such that it can only be inserted into the cylinder 122 in one orientation whereby the first divot 130, the second divot 136, and the opening 134 are aligned. Consequently, the sphere 132 is either partially in the first divot 130 or partially in the second divot 136.

To attach the tool 10*d* to the ball-slide clamping mechanism 120, the slide 128 is pulled upward from its downwardly-biased position to allow the sphere 134 to enter divot 130 in the slide 128. The tool 10*d* is then inserted into the cylinder 122. The slide 128 is released such that the spring 126 forces the slide 128 downwardly and the sphere 132 is pushed inwardly by the inner wall of the slide 128. The sphere 132 then is forced into second divot 136 which locks the tool 10*d* into position. To remove the tool 10*d*, the slide 128 is pulled upwardly so that the sphere 132 enters the first divot 130 which frees the sphere 132 from the second divot 136 thereby releasing the tool 10*a*.

FIG. 5C illustrates a common three-jaw chuck device 150 clamping osteotome tool 40*d* from FIG. 2D. The three jaws 152 grasp the upper portion of the tool 40*d* and hold it firmly in place. The jaws 152 fit within a collar 154 which is coupled to a chuck 156. The shaft 92 of the driving mechanism 80 attaches to the upper end of the chuck 156.

When the chuck 156 is rotated relative to the collar 154, the three jaws 152 either spread apart or come together, depending on the direction of rotation. The chuck 156 includes gear teeth 158 at its lower end to which a geared key engages to help rotate the chuck 156 relative the collar 154 to open and close the jaws 152. The collar 154 also includes a hole 160 in which the geared key can be inserted to assist in this task. Thus, the tool 40*d* can be attached through the clinician's manual rotation of the chuck 156 relative to the collar 154 or the clinician can use a key to perform this task.

In FIGS. 5A–5C, the driving mechanism 80 includes the shaft 92 which urges the tool downwardly into the bone. The movement of the shaft 92 and, therefore, the tool can be continuous such that the insertion occurs at a constant rate. Alternatively, the insertion can be stepped in that the shaft 92 moves the tool for a predetermined time interval at a predetermined rate and then stops, or slows, before resuming to that predetermined rate. Thus, the tool is incrementally inserted into the bone.

In addition, the driving mechanism 80 may also include a high-frequency vibration transducer, such as a piezoelectric transducer or an ultrasonic transducer. As the tool is being inserted, high-frequency waves act upon the tool through the shaft 92 to assist in the insertion process. The frequency and amplitude of the waves are selected to provide ease of insertion but preferably produce minimal heat at the interface between the tool and the bone tissue. In one preferred embodiment, the amplitude is low (less than about 1.0 mm) and the frequency is high (e.g. 500 Hz). Thus, less axial force from the driving mechanism 80 is needed to insert the tool into the bone.

FIGS. 6A and 6B illustrate a reciprocating driving mechanism 180 that is inserting tool 10*a*, shown in FIG. 1A, into bone tissue 70 to form a bore. The driving mechanism 180 includes a shaft 192 which reciprocates an engaging mechanism 194 that is attached to the shaft 192. The engaging mechanism 194 taps, or hammers, the tool 10*a* into the bone tissue 70. FIG. 6A shows the shaft 192 at the lower end of its stroke as the engaging mechanism 194 contacts the tool 10*a*. FIG. 6B depicts the shaft 192 at the upper end of its stroke when it is not in contact with tool 10*a*. Thus, the primary difference between the clamping mechanisms of FIGS. 5A–5C and the engaging mechanism 194 of FIGS. 6A–6B is that the clamping mechanisms remain attached to the tool at all times during operation while the engaging mechanism 194 does not. In the configuration of FIGS. 6A and 6B, it may be necessary to pull the tool 10a from the bore after the driving mechanism 180 fully inserts the tool 10a.

Although the upper portion of the tool 10a has a flat surface, it may have a curved surface to minimize the amount of off-axis tapping causing the angle of insertion of the tool 10a to vary. The inner surface of the engaging mechanism 194 may also include a curved surface. Additionally, the entire engaging mechanism 194 can be a variety of shapes. Thus, it can surround the tool 10a by having an internal cavity, as shown, or it can be a flat surface. Additionally, the base portion 24a of the tool 10a can have a polygonal cross-section with the engaging mechanism having a corresponding socket.

FIG. 7 illustrates a solenoid 200 which is used as the driving mechanism. The solenoid 200 includes an armature 202 which moves between two positions (one showed in dashed lines) when the coil 204 is energized and deenergized. Typically, a spring biases the armature 202 to the deenergized position. Armature 202 would act as, or be coupled to, the shaft 92 or 192 of FIGS. 5–6 to move the tool into the bore.

Typically, the armature 202 moves rapidly between the two positions with transition times being less than about 0.5 second. Thus, it serves as a useful driving mechanism for the reciprocating-type driving mechanism 180 shown in FIGS. 6A and 6B. Thus, energizing and de-energizing the coil 204 produces this rapid reciprocating motion.

Also, the movement of the armature 202 can be designed to produce a slow movement between the two positions. For example, the current through the coil 204 can be slowly ramped-up to produce this slow movement. Alternatively, the armature 202 can be dampened by a spring or a hydraulic device to resist, but slowly yield to the electromagnetic force produced by the coil 204. Thus, the solenoid 200 could also serve as the driving mechanism 80 shown in FIGS. 5A–5C.

Figure 8:
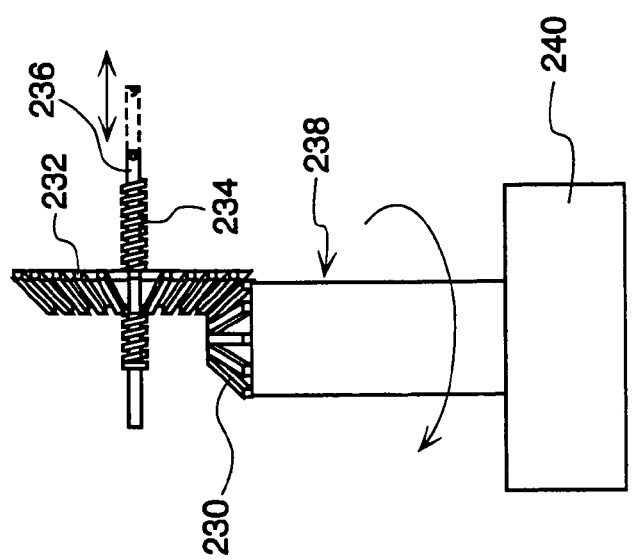
FIG. 8 illustrates an electric motor as the driving mechanism which produces translational motion through a gear configuration.

FIG. 8 illustrates one of many possible meshed gear configurations. In FIG. 8, a pair of beveled gears 230 and 232 drives a worm gear 234 on post 236. A shaft 238 attached to the first beveled gear 230 is driven by an electric motor 240 (AC or DC). As the first beveled gear 230 turns the second beveled gear 232, a worm gear 234 engages internal threads (not shown) within the second beveled gear 232 to move post 236 between the two positions (one shown in dashed lines). Post 236 is coupled to, or acts as, shaft 92 in the driving mechanism 80 of FIGS. 1–5. Another meshed-gear configuration would simply rotate a nut-type structure having internal threads around an externally threaded shaft (like post 236) to cause longitudinal movement of the shaft. One advantage of the gear configuration illustrated in FIG. 8 as well as other meshed-gear configurations is that the depth of penetration could be accurately controlled since there would be a fixed relationship between the penetration depth of the tool and the number of revolutions of the shaft 238 coupled to the electric motor 240.

To produce a rapid reciprocating motion, the electric motor 240 produces oscillatory electrical power to rotate shaft 238 in both directions which, in turn, moves the post 236 in both directions. Thus, the gear configuration of FIG. 8 can also be used to produce the reciprocating motion described with reference to the driving mechanism 180 of FIGS. 6A and 6B.

FIG. 9 illustrates one of many possible cam configurations that produce axial movement of the tool. The electric motor 240, the same as the one shown in FIG. 8, drives cam cylinder 250 via a shaft 241. Cam cylinder 250 has an upper surface 251 near the electric motor 240 and a lower surface 253. The lower surface 253 is, in essence, a cam in that it is irregularly shaped with a cam drop 254.

Member 260 is shown in a exploded view away from cam cylinder 250 but in operation is immediately adjacent the cam cylinder 250. Member 260 includes an upper surface 261 corresponding to lower surface 253 of the cam cylinder 250. A cam drop 262 matches the cam drop 254 of the cam cylinder 250. A spring 264, coupled to member 260, biases member 260 upward to engage the cam cylinder 250. Member 260, which typically does not rotate, also has a post 268 to which it is coupled.

When the electric motor 240 rotates the cam cylinder 250 such that the opposing cam drops 262 and 254 move away from each other, the lower surface 253 of the cam cylinder 250 engages the upper surface 261 of the member 260 forcing member 260 downward against the bias of the spring 264. Consequently, post 268, which is coupled to, or acts as, shaft 92 of the driving mechanism 80 of FIGS. 5A–5C, moves downward. Because the amount of the axial movement of post 92 is the same as the length of cam drop 254, the amount of movement can be accurately controlled. Additionally, if a only portion of the maximum axial movement is needed (e.g. 75%), then the amount of rotation of the cam cylinder 250 is limited to 75% of one revolution (i.e. 270°). Again, the amount of axial movement of post 268 can be accurately controlled. And, the spring 264, which determines the force of insertion, is selected accordingly.

If the reciprocating movement of FIGS. 6A and 6B is desired, the cam cylinder 260 can be rotated continuously. The action of the spring 264 maintains the position of the action member 260 in its upwardly biased position after one full revolution. The frequency of the reciprocating motion corresponds to the angular speed of the shaft 241.

FIG. 10 illustrates the electric motor 240 rotating a cam cylinder 280 that has a small cam 282 on its lower surface. The small cam 282 engages a projecting surface 284 located on a plate 286 attached to rod 288. The plate 286 is biased in the upward position by a spring 290 attached to structure 292. As the cam cylinder 280 rotates, the rod 288 reciprocates between two positions (one shown in dashed lines). To drive the osteotome tool, rod 288 is coupled to, or acts as, shaft 192 of the driving mechanism 180 of FIGS. 6A and 6B.

FIG. 11 illustrates a piezoelectric vibrator 300 which imparts reciprocating or vibrational motion to the osteotome tool. The vibrator 300 includes a transducer element 302 to which is attached two electrodes 304 that are coupled to an electrical source 306. A cone-shaped mechanical coupling component 308 is attached to the transducer element 302 and has an acoustical length that causes it to vibrate when the transducer element 302 is actuated. When electrical oscillations are produced by the electrical source 306, the transducer element 302 oscillates and causes the coupling component 308 to vibrate. A rod 310 affixed to the end of the coupling component 308 then reciprocates between two positions (one shown in dashed lines). Variations in the amplitude and frequency provided by electrical source 306 cause variations in the movement of the rod 310. Thus, rod 310 is coupled to, or acts as, shaft 192 of the driving mechanism 180 of FIGS. 6A and 6B.

The piezoelectric vibrator 300 can also be used to provide high-frequency vibrations. Thus, it can be used by itself, or in tandem with another type of driving mechanism that causes the axial movement of the tool. The piezoelectric vibrator 300 would provide the high-frequency waves while the other driving mechanism would provide the axial movement. As stated previously, the high-frequency waves would assist in the insertion of the tool.

Another device which can provide vibrational movement to the tool is a harmonic generator which is often used to power a scalpel. The harmonic generator provides ultrasonic energy which operates at a very high frequency (i.e. about 50 kHz) in the longitudinal direction of the tool via ultrasonic transducer. Generally, the amplitude applied to the tool when using such a harmonic generator is between 20 and 200 microns. The ultrasonic motion of the tool has extremely high acceleration which converts mechanical energy into thermal energy in a very localized region. The heat associated with this thermal energy can be used to reduce or eliminate some of the bleeding which occurs during the insertion process. The coagulation which results from this motion may be desired in situations where excessive bleeding is a concern since in most cases, minimal heat is desired so as to not damage the bone tissue. One example of a harmonic generator that produces ultrasonic energy is described in U.S. Pat. No. 5,026,387 which is herein incorporated by reference in its entirety.

Figure 12:
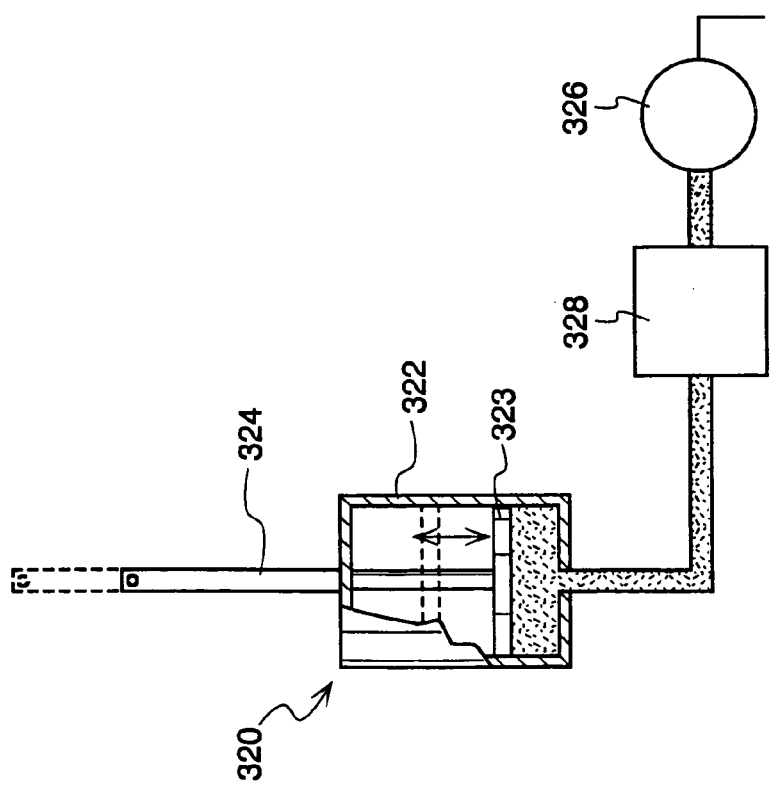
FIG. 12 illustrates a hydraulically-powered driving mechanism.

FIG. 12 illustrates a hydraulically-actuated driving mechanism 320 having a cylinder 322 contains a piston 323 that is connected to a rod 324. A pump device 326 acts upon the fluid to move it into and out of the cylinder 320. A fluid accumulator 328 may also be present within the hydraulically-actuated driving mechanism 320. The pump 326 may be a hand pump or powered pump. As the fluid moves into the lower portion of the cylinder 322, the piston 323 moves upward thereby moving rod 324 upward. Thus, rod 324 is coupled to, or acts as, shaft 92 of the driving mechanism 80 of FIGS. 5A to 5C described above. A structure similar to the hydraulically-actuated driving mechanism 320 which works on pressure produced by air or other gases (i.e. pneumatically-actuated system) could be utilized.

Figure 13:
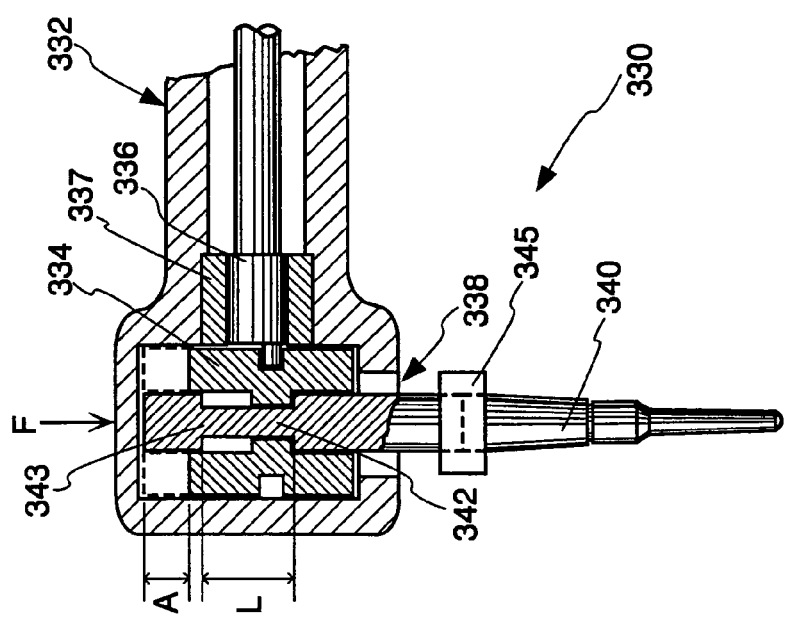
FIG. 13 illustrates a dental hand piece driving the osteotome tool.

FIG. 13 illustrates a driving mechanism 330 which utilizes a common dental hand piece 332. The dental hand piece 332 includes a driving component 334 which oscillates between two positions due to the rotation of a shaft 336. As shown, the shaft 336 is coupled to the driving component 334 by a yoke-type configuration although a gear configuration or cam configuration could work just as well. The shaft 336 is supported within the dental hand piece 332 by a bearing element 337 that is near the driving component 334.

The bottom side of the dental hand piece 332 includes an opening 338 in which a tool 340 can be inserted. The tool 340 is an osteotome tool as described previously which compacts the bone tissue in the bore which it is creating. The tool 340 includes a narrow neck portion 342 above which resides a head portion 343. The tool 340 also includes a ring 345 which prohibits the insertion of the tool 340 beyond a predetermined depth in the bone tissue. In other words, ring 345 is a stop mechanism which engages the exterior surface of the bone tissue thereby allowing only the lower segment of the tool 340 below the ring 345 to be inserted into the bone.

The amount of oscillation in the tool 340 is a function of the amplitude A at which the driving component 334 is oscillating. The motion of the tool 340 is also a function of the length L of the narrow neck portion 342. Because the frequency at which the driving component 334 operates is a function of the angular velocity of the shaft 336, the frequency at which the tool 340 oscillates can be controlled. The distance which the tool 340 travels in one-half cycle (i.e. one path down or up) is a function of the amplitude A at which the driving component 334 operates. Additionally, the distance which the tool 340 travels in one-half cycle is a function of the length L of the narrow neck portion 342 of the tool 340. Thus, the distance the tool travels can be controlled as well. By means of an example, the frequency may be in the range of 500 Hz to 1000 Hz and the distance traveled may be on the order of a millimeter or less.

In FIG. 13, the force F that is being exerted on the driving mechanism 330 and then transferred to the tool 340 is produced by the clinician. Thus, the tool is moving into the bore under the force of the clinician while vibrating at a know rate to assist in the insertion process.

The various driving mechanisms described can provide two types of motion. First, these mechanism can be used to provide oscillatory or vibrational motion to the tool to assist in the insertion of the tool. The primary force to insert the tool would then be the force applied by the clinician to the driving mechanism. Alternatively, the driving mechanism may provide for translational movement to insert the tool to the proper position within the bore. In yet another alternative, the driving mechanism may provide both translation and vibrational energy.

Figure 14:
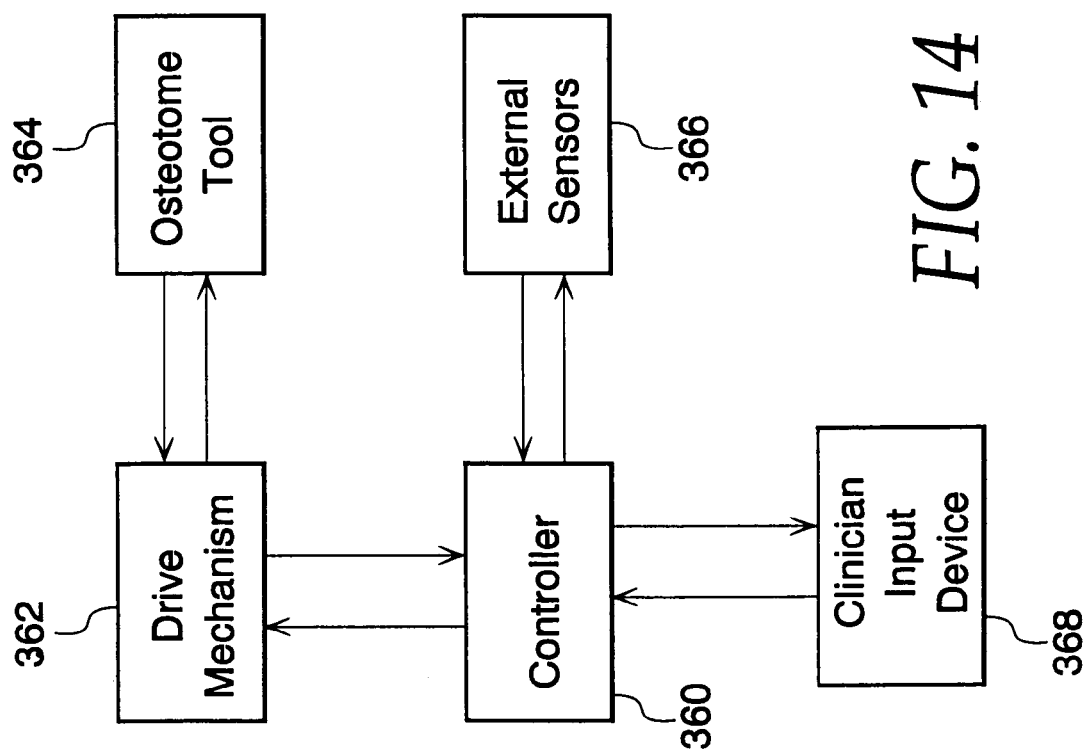
FIG. 14 illustrates a power-driven osteotome system with a controller.

FIGS. 7–13 illustrate various driving mechanisms which could be used to insert an osteotome tool into a bone and create a bore for an implant. Because the characteristics of the movement of the tool (e.g. depth of insertion, the force of insertion, the frequency of insertion, etc.) are important, the operation of the driving mechanism may be controlled by a controller. FIG. 14 illustrates, in block diagram form, a power-driven osteotome system 350. The system 350 includes a controller 360 which is coupled to the drive mechanism 362. The controller 360 applies power to the drive mechanism 362 which, in turn, acts upon the tool 364 to force it into the bone. The drive mechanism 362 may be any type of drive mechanism including those described in FIGS. 7–13 and the tool 364 may be any type of osteotome tool including those described in FIGS. 1–4. The tool 364 is releasably coupled to the drive mechanism 362 through various methods including those disclosed with reference to FIGS. 5–6.

The controller 360 may monitor the drive mechanism 362. For example, if the drive mechanism 362 includes the electric motor 240 of FIGS. 8–10, the controller 360 may sense an angular displacement sensor, such as an encoder, within the motor 240 to determine the angular position of the shaft of the motor 240. This can be used to determine the angular speed which corresponds to the reciprocating movement of the tool 364. An angular displacement sensor, such as an encoder, can also be useful in the configurations of FIGS. 8–9 to determine the amount of rotation of the shaft when only a portion (e.g. 50%) of one revolution is needed. Thus, the depth of insertion can be controlled.

The controller 360 can also be coupled to external sensors 366 which relay signals to the controller 360. For example, an electrode could be placed immediately adjacent to the site at which the implant is to be inserted. The osteotome tools 364 have a corresponding electrode which is cantilevered from the outer surface of the tool at a point along its length corresponding to the appropriate depth of insertion. When the tool is pushed into the bone and the two electrodes touch, a signal is relayed to the controller 360 which stops the drive mechanism. Thus, the depth of insertion is controlled.

The controller 360 could monitor external sensors 366 solely within the tool. For example, the tool may have optical sensors at known points along its length. When an optical sensor enters the bone, the controller 366 senses the exact depth at which the tool has been inserted. Thus, the controller 366 stops the drive mechanism when the optical sensor associated with the desired depth encounters the bone. The optical sensor could be replaced by pressure sensor since the surface of the implant will become stressed when it engages bone.

The controller 360 also is preferably coupled to a clinician input device 368 which allows the clinician to select various parameters related to the operation of the drive mechanism 362. For example, the clinician may select the depth of insertion, the frequency of the reciprocation motion, or the amplitude of the reciprocating motion. The clinician input device 368 also includes simple on/off buttons to allow the clinician to turn the drive mechanism 362 on and off.

To further assist in the insertion of the tools, the drive mechanism which remains coupled to the tool (FIGS. 5A–5C) can also provide for a minimal rotation of the tool. Thus, a point along the surface of the tool moves in a helical fashion as it is inserted into the bore and rotated simultaneously. The armature 202 of the solenoid 200 in FIG. 7, the rod 310 of the piezoelectric transducer 300 of FIG. 11, or the rod 324 of the hydraulic driving mechanism 320 of FIG. 13 could be coupled, via gears, to an electric motor to provide this rotation. Alternatively, the cammed driving mechanism of FIG. 9 could be rotated in a direction opposite to the arrow shown causing the corresponding cam drops 254, 262 to engage and allow for this simple rotation. This may require the member 260 to include a ratcheting mechanism to permit its rotation in only one direction so that the member 260 remains non-rotational when undergoing the translation motion. And, the gear configuration of FIG. 8 can also be used to supply rotational movement.

Although the tools and driving mechanism have been primarily described with respect to the human jawbone, this technique can be used in nearly all bone tissue. In other words, this technique has applications in surgery where an anchoring device is installed in bone tissue other than when a dental implant is placed in the jawbone.

What is claimed is:

1. A device for developing a bore in living bone for receiving a screw-type dental implant, said device comprising:
    an osteotome tool having a central axis, a lower end, an upper end, and an outer surface extending from said lower end to said upper end, said central axis being located entirely within said outer surface between said upper end and said lower end, said outer surface for compacting bone to define an elongated bore having a length that is sized to receive said screw-type dental implant, said osteotome tool has a cross-section that increases from said lower end to said upper end and depth markings between said lower end and said upper end;
    a driving mechanism including means for interchangeably coupling said driving mechanism to said upper end of said osteotome tool, said driving mechanism including a piezoelectric transducer element imparting a vibrational motion to said osteotome tool; and
    a power source for delivering electrical power to said driving mechanism.

2. The device of claim 1, wherein said coupling means includes means for quickly releasing and attaching said tool from said driving mechanism.

3. The device of claim 1, wherein said vibrational motion is primarily in the direction of said central axis of said osteotome tool.

4. The device of claim 1, wherein said driving mechanism includes a drive rod between said piezoelectric transducer and said coupling means.

5. The device of claim 1, wherein said driving mechanism includes a cone-shaped mechanical coupling component.

6. The device of claim 1, wherein said osteotome tool has at least one segment with a constant cross-section.

7. The device of claim 1, wherein said coupling means is selected from the group consisting of a spring element, a pin element extending into said osteotome tool, a screw element extending into said osteotome tool, a ball-slot clamping mechanism, a ball-slide clamping mechanism, and a three jaw-chuck device.

8. A method for installing an implant in an elongated bore in a living bone, said method comprising the steps of:
    providing an osteotome tool having a central axis, a lower end, an upper end, and an engaging surface between said lower and upper ends;
    providing a driving mechanism including a piezoelectric transducer element capable of producing vibrational motion;
    coupling said driving mechanism to said osteotome tool;
    powering said driving mechanism to actuate said piezoelectric transducer element while engaging said living bone with said engaging surface to develop said elongated bore, said elongated bore being defined by bone tissue and having a known length and width dimension corresponding to the length and width dimension of the said engaging surface; and
    installing said implant into said elongated bore, said implant having a length corresponding to said length of said elongated bore.

9. The method of claim 8, wherein said engaging surface has a sequence of regions from said lower end to said upper end that increase in cross-sectional area.

10. The method of claim 8, wherein said tool has regions of a constant diameter.

11. The method of claim 8, wherein said piezoelectric transducer element oscillates when electrical oscillations are produced by said electrical power.

12. The method of claim 8, wherein said vibrational motion occurs along said central axis of said osteotome tool.

13. The method of claim 8, wherein said vibrational motion has a low amplitude of less than about 1.0 mm.

14. The method of claim 8, wherein said vibrational motion has a frequency of about 500 Hz.

15. The method of claim 8, wherein said vibrational motion is varied by changes to a frequency and an amplitude of electric power supplied to said piezoelectric transducer.

16. A device for developing in living bone an elongated bore that is defined by bone tissue with increased density, said device comprising:
    a compaction tool having a central axis, a lower end, and upper end, and a bone engaging surface for displacing bone tissue that is initially in the area defined by said bore primarily in the radial direction with respect to said central axis, said bone-engaging surface having depth markings so as to determine a depth of insertion into said elongated bore; and
    a driving mechanism including means for coupling said driving mechanism to said tool, said driving mechanism further including means for vibrationally moving said tool.

17. The device of claim 16, wherein said compaction tool is tapered from said upper end to said lower end.

18. The device of claim 16, wherein said vibrational movement is in a direction of said central axis.

19. The device of claim 16, wherein said osteotome tool has at least one segment with a constant cross-section.

20. A method for developing an elongated bore in a living bone for receiving a dental implant, said method comprising the steps of:
provide an osteotome tool having a central axis, a lower end, an upper end, and an engaging surface between said lower and upper ends;
providing a driving mechanism capable of producing reciprocating motion;
coupling said driving mechanism to said osteotome tool;
engaging said osteotome tool with said living bone, while said osteotome tool is undergoing reciprocating motion to create said elongated bore, said elongated bore having dimensions defined by dimensions of said engaging surface of said osteotome tool, said osteotome tool simultaneously and continuously engages said living bone substantially along an entire length of said bore while the bore is created; and
using a power-driven mechanism to install said dental implant into said elongated bore.

21. The method of claim 20, wherein said reciprocating motion is in a direction of along said central axis.

22. The method of claim 20, wherein said osteotome tool is tapered from said upper end to said lower end.

23. The method of claim 20, wherein said osteotome tool incrementally compacts said living bone while developing said bore.

24. The method of claim 20, further including the step of developing a pilot hole, and said step of engaging includes inserting said tool into said pilot hole.

25. A device for developing an elongated bore in living bone, comprising:
a tool having a central axis, a lower end, and an upper end, said tool having a cutting edge at said lower end and a bone engaging surface above said cutting edge for displacing bone tissue primarily in the radial direction with respect to said central axis, said cutting edge is configured to cut bone around a circumference of said elongated bore and maintain a substantial portion of said bone within said elongated bore, said bone engaging surface including depth markings for determining a depth of insertion into said elongate bore; and
a driving mechanism coupled to said tool and producing vibrational movement to said tool.

26. The device of claim 25, wherein said driving mechanism includes a piezoelectric device.

27. The device of claim 25, wherein said bone engaging surface has a gradually expanding region behind said cutting edge.

28. The device of claim 27, wherein said gradually expanding region is directly behind said cutting edge.

29. The device of claim 25, wherein said tool includes conduits for passing a lubricating fluid.

30. The device of claim 25, wherein said cutting edge is located in a generally circular configuration.

31. The device of claim 30, wherein said tool has a concave surface within said circular configuration.

32. A method for developing a bore in living bone, comprising:
creating a pilot opening at a location in said living bone where said bore is desired;
engaging a tool with a piezoelectric component, said tool having a lower cutting edge and an expanding cross-sectional region above said lower cutting edge, said tool including depth markings on an outer surface thereof for determining a depth of insertion into said bore;
inserting said cutting edge into said pilot opening of said bone;
as said tool is inserted deeper into said opening, cutting said bone with said cutting edge while simultaneously compacting said bone with said expanding cross-sectional region.

33. The method of claim 32, wherein said tool has regions of constant diameter.

34. The method of claim 32, wherein said piezoelectric component provides vibrational motion along a central axis of said tool.

35. The method of claim 34, wherein said vibrational motion has a frequency of about 500 Hz.

36. A method for developing a bore in a living bone, comprising:
providing a tool having a central axis, a cutting edge at a lowermost end and being generally perpendicular to said central axis, an engaging surface above said cutting edge for compacting said living bone, and an upper end positioned opposite of said lowermost end, said central axis extending between said lowermost end and said upper end;
providing a driving mechanism capable of producing vibrational motion along said central axis;
coupling said upper end of said driving mechanism to said tool; and
powering said driving mechanism while engaging said living bone with said cutting edge to develop said bore, said engaging occurring as said central axis is generally perpendicular to said living bone adjacent to said bore.

37. The method of claim 36, wherein said driving mechanism includes a piezoelectric device.

38. The method of claim 36, wherein said powering said driving mechanism includes applying electrical power to said piezoelectric device at a selective frequency and amplitude.

39. A dental system for developing a bore in living bone that is to receive a screw-type dental implant, said device comprising:
a screw-type dental implant;
an osteotome tool having a central axis, a cutting edge at said lowermost end, and a bone-compacting surface directly above said lowermost end for compacting bone in a radial direction with respect to said central axis, said bone-compacting surface having a generally circular cross-section such that said bone-compacting surface compacts bone around said tool and being dimensioned in length to provide said bore with a dimension for threadably receiving said screw-type dental implant;
a driving mechanism including means for interchangeably coupling said driving mechanism to said osteotome tool, said driving mechanism including a piezoelectric transducer element imparting a vibrational motion to said osteotome tool; and
a power source for delivering electrical power to said driving mechanism.

40. The dental system of claim 39, wherein said osteotome tool gradually tapers outwardly.

41. The dental system of claim 39, wherein said osteotome tool has a transverse dimension along its length that generally corresponds to a diameter of said dental implant.

42. A method for installing a dental implant into a bore in a living bone, said method comprising the steps of:

providing an osteotome tool having a central axis, a generally circular cross-section, a lower end, an upper end, and an engaging surface between said lower and upper ends;

providing a driving mechanism including a piezoelectric transducer element capable of producing vibrational motion;

coupling said driving mechanism to said osteotome tool;

powering said driving mechanism to actuate said piezoelectric transducer element;

engaging said living bone with said osteotome tool to develop said bore, said bore having a generally circular cross-section; and screwing said dental implant into said bore.

43. The method of claim 42, wherein said engaging surface has a sequence of regions from said lower end to said upper end that increase in cross-sectional area.

44. The method of claim 42, wherein said tool has regions of a constant diameter.

45. A set of components for installing a screw-type dental implant in a bore that is defined by bone tissue with increased density, said set of components comprising:

a screw-type dental implant having an exterior surface for engaging said bone tissue;

a compaction tool having a central axis, a lower end, and upper end, and a bone engaging surface for displacing bone tissue that is initially in the area defined by said bore primarily in the radial direction with respect to said central axis, said compaction tool having a generally circular cross section for producing a known dimension in said bore for receiving said screw-type dental implant; and a driving mechanism including means for coupling said driving mechanism to said tool, said driving mechanism further including means for vibrationally moving said tool while in said bore; and wherein said screw-type dental implant for being threadably installed in said bore after said compaction tool creates said bore.

46. The set of components of claim 45, wherein said compaction tool is tapered from said upper end to said lower end.

47. A set of components for installing a screw-type dental implant in a bore in living bone for receiving a dental implant, comprising:

a screw-type dental implant having an exterior surface that engages said bone tissue after said tool produces said bore;

a tool having a central axis, a lower end, and an upper end, said tool having a bone engaging surface above said lower end for displacing bone tissue primarily in the radial direction with respect to said central axis, said tool having a generally circular cross-section with a transverse dimension that produces a bore having a predictable dimension for threadably receiving said screw-type dental implant; and a driving mechanism providing vibrational movement to said tool.

48. The set of components of claim 47, wherein said driving mechanism includes a piezoelectric device.

49. The set of components of claim 47, wherein said bone engaging surface has a gradually expanding region behind said lower end.

50. The set of components of claim 47, wherein said tool is configured to maintain a substantial portion of bone acted upon by said tool within said bore.

* * * * *